(12) United States Patent
Tanase et al.

(10) Patent No.: US 7,723,254 B2
(45) Date of Patent: May 25, 2010

(54) MAGNESIUM COMPOUND, SOLID CATALYST COMPONENT, OLEFIN POLYMERIZATION CATALYST, AND METHOD FOR PRODUCING OLEFIN POLYMER

(75) Inventors: Shojiro Tanase, Ichihara (JP); Nobuhiro Yabunouchi, Sodegaura (JP); Takehito Konakazawa, Ichihara (JP); Takanori Sadashima, Sumida-ku (JP); Kiyokazu Katayama, Ichihara (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 12/404,408

(22) Filed: Mar. 16, 2009

(65) Prior Publication Data

US 2009/0181845 A1 Jul. 16, 2009

Related U.S. Application Data

(62) Division of application No. 11/573,045, filed as application No. PCT/JP2005/014176 on Aug. 3, 2005, now abandoned.

(30) Foreign Application Priority Data

Aug. 3, 2004 (JP) .............................. 2004-226820

(51) Int. Cl.
C08F 4/02 (2006.01)
C08F 4/64 (2006.01)
(52) U.S. Cl. ........................ 502/115; 502/104; 502/111; 502/118; 502/171; 526/124.3
(58) Field of Classification Search ................. 502/104, 502/111, 115, 118, 171; 526/124.3
See application file for complete search history.

(56) References Cited

U.S. PATENT DOCUMENTS

| | | | | |
|---|---|---|---|---|
| 4,414,132 A * | 11/1983 | Goodall et al. | ............... | 502/104 |
| 4,496,660 A | 1/1985 | Gessell et al. | | |
| 4,959,336 A * | 9/1990 | Job | ......................... | 502/107 |
| 6,777,365 B2 * | 8/2004 | Tanase et al. | ............... | 502/115 |
| 7,387,979 B2 * | 6/2008 | Tanase et al. | ............... | 502/102 |
| 2009/0148702 A1 * | 6/2009 | Dietz et al. | .................. | 428/402 |

FOREIGN PATENT DOCUMENTS

| | | |
|---|---|---|
| JP | 56-000811 | 1/1981 |
| JP | 63 280707 | 11/1988 |
| JP | 4 130107 | 5/1992 |
| JP | 4 178406 | 6/1992 |
| JP | 2000 44620 | 2/2000 |
| JP | 2001 233879 | 8/2001 |
| JP | 2003 342217 | 12/2003 |
| WO | WO 01/00633 | 1/2001 |

* cited by examiner

Primary Examiner—Caixia Lu
(74) Attorney, Agent, or Firm—Oblon, Spivak, McClelland, Maier & Neustadt, L.L.P.

(57) ABSTRACT

A method of producing a magnesium compound by reacting the following components (i), (ii) and (iii):
(i) metal magnesium
(ii) an alcohol
(iii) a metal dihalide compound represented by the general formula (I) containing at least 0.001 mole of M relative to one mole of magnesium of the metal magnesium (i)

$$MX_2 \qquad (I)$$

where X is a halogen atom and M is Mn, Fe, Co or Zn.

12 Claims, 3 Drawing Sheets

MAGNESIUM COMPOUND, SOLID CATALYST COMPONENT, OLEFIN POLYMERIZATION CATALYST, AND METHOD FOR PRODUCING OLEFIN POLYMER

REFERENCE TO PRIOR APPLICATIONS

This application is a Divisional application of U.S. Ser. No. 11/573,045, filed Feb. 1, 2007, now pending; which is a 371 of PCT/JP05/14176, filed Aug. 3, 2005; and claims priority to Japan patent application 2004-226820, filed Aug. 3, 2004.

TECHNICAL FIELD

The invention relates to a magnesium compound which is useful for homopolymerization or copolymerization of ethylene and an α-olefin, a solid catalyst component, a catalyst for olefin polymerization and a method of producing an olefin polymer.

TECHNICAL BACKGROUND

Hitherto, magnesium chloride and magnesium alkoxides have been widely used as a support material without being milled in the field of catalysts for olefin polymerization, specifically the homopolymerization or copolymerization of ethylene, propylene or the like. This may improve the catalyst activity and the morphology of polymer powder.

For example, for improving an obtained polymer in morphology including particle size, form, etc., there are known a method in which a magnesium compound is supported on an inorganic oxide such as silica (JP-A-S63-280707) and a method in which a magnesium compound once dissolved in a solvent such as an alcohol is precipitated again and the precipitate is used (JP-A-S56-000811). However, these methods include very complicated steps, since they require the procedures of supporting, dissolving and precipitating a magnesium compound. Further, these methods have a defect in that the catalyst is poor in performance stability.

The method of using as a support of catalysts a magnesium compound obtained by reacting metal magnesium, an alcohol such as ethanol and a certain amount of halogen (JP-A-H4-130107) has been developed. However, it has a problem in the point that the size and form of the polymer powder particle obtained depends on the conditions. For example, it does not permit omission of a pelletizing step and may not enable a copolymer of ethylene to be produced with sufficiently high efficiency.

In view of the above-mentioned problems, an object of the invention is to provide a magnesium compound, solid catalyst component and catalyst for olefin polymerization that exhibits high activity and can give an olefin polymer excellent in morphology of the polymer powder with a high stereoregularity.

Further, an object of the invention is to provide a method of producing an olefin polymer that can give an olefin polymer excellent in morphology of the polymer powder with a high stereoregularity.

DISCLOSURE OF THE INVENTION

The present inventors conducted various studies through which they found that the above objects can be attained by producing a magnesium compound using a specific metal dihalide compound.

The invention provides the following magnesium compound, solid catalyst component, catalyst for olefin polymerization and method of producing olefin polymer.

1. A magnesium compound obtained by reacting the following components (i), (ii) and (iii):
   (i) metal magnesium
   (ii) an alcohol
   (iii) a metal dihalide compound represented by the general formula (I) containing at least 0.001 mole of M relative to one mole of magnesium of the metal magnesium (i)

$$MX_2 \quad (I)$$

where X is a halogen atom and M is Mn, Fe, Co or Zn.

2. The magnesium compound according to 1, wherein the metal dihalide compound (iii) is manganese dichloride.
3. The magnesium compound according to 1, wherein the metal dihalide compound (iii) is iron dichloride.
4. The magnesium compound according to 1, wherein the metal dihalide compound (iii) is cobalt dichloride.
5. The magnesium compound according to any one of 1 to 4 which is obtained by reacting a halogen and/or a halogen-containing compound (iv) containing at least 0.0001 gram atom of a halogen atom relative to one gram atom of magnesium of the metal magnesium (i) in addition to the components (i), (ii) and (iii), the halogen-containing compound not including the metal dihalide compound (iii)

6. The magnesium compound according to 5, wherein the halogen (iv) is iodine.
7. The magnesium compound according to 5, wherein the halogen-containing compound (iv) is magnesium dichloride.
8. A solid magnesium compound which has an average particle diameter ($D_{50}$) of 50 μm or more, a sphericity (Sp) represented by the expression (1) of 1.60 or less and a smoothness (Sm) represented by the expression (2) of 1.20 or less:

$$Sp=(L^1/L^2)^3 \quad (1)$$

where $L^1$ is the longest diameter of a projection view of a magnesium compound particle determined by photographing with a scanning electron microscope and thereafter performing image-processing, and $L^2$ is the diameter of a circle which has an area equal to the projection area of the magnesium compound particle;

$$Sm=(L^3/L^4)^3 \quad (2)$$

where $L^3$ is the circumferential length of a projection view of a magnesium compound particle determined by photographing with a scanning electron microscope and thereafter performing image-processing, and $L^4$ is the circumferential length of an ellipse which has an area equal to the projection area of the magnesium compound particle and which is approximated to the profile of the magnesium compound particle such that when the magnesium compound particle is superimposed on the ellipse, the sum of the areas inside and outside the profile of the ellipse among the sections surrounded by the profile of the magnesium compound particle and the profile of the ellipse becomes minimum.

9. A solid magnesium compound which has an average particle diameter ($D_{50}$) of 50 μm or more, a sphericity (Sp) represented by the expression (1) of 1.60 or less, a depth of surface hollows (Lsh) of 3 μm or more, and a surface where small spheres connect with each other like a bunch of grapes:

$$Sp=(L^1/L^2)^3 \tag{1}$$

where $L^1$ is the longest diameter of a projection view of a magnesium compound particle determined by photographing with a scanning electron microscope and thereafter performing image-processing, and $L^2$ is the diameter of a circle which has an area equal to the projection area of the magnesium compound particle.

10. A solid catalyst component obtained by reacting the following components (a) and (b):
(a) the magnesium compound according to any one of 1 to 9
(b) a titanium compound represented by the general formula (II)

$$Ti(OR)_nX_{4-n} \tag{II}$$

where X is a halogen atom, R is a hydrocarbon group having from 1 to 10 carbon atoms, a plurality of which are the same as or different from each other, and n is an integer of from 0 to 4.

11. The solid catalyst component according to 10 obtained by reacting the following components (c) and/or (d) in addition to the components (a) and (b):
(c) a halide compound
(d) an electron donating compound.

12. The solid catalyst component according to 11, wherein the halogen compound (c) is silicon tetrachloride.

13. A catalyst for olefin polymerization comprising the following components (A) and (B), or
the following components (A), (B) and (C):
(A) the solid catalyst component according to any one of 10 to 12
(B) an organometallic compound
(C) an electron donating compound.

14. A method of producing an olefin polymer using the catalyst for olefin polymerization according to 13.

The invention provides a magnesium compound, solid catalyst component and catalyst for olefin polymerization that exhibits high activity and can give an olefin polymer excellent in morphology of the polymer powder with a high stereoregularity.

The invention provides a method of producing an olefin polymer that gives an olefin polymer excellent in morphology of polymer powder with a high stereoregularity.

BEST MODE FOR CARRYING OUT THE INVENTION

Figure 1:
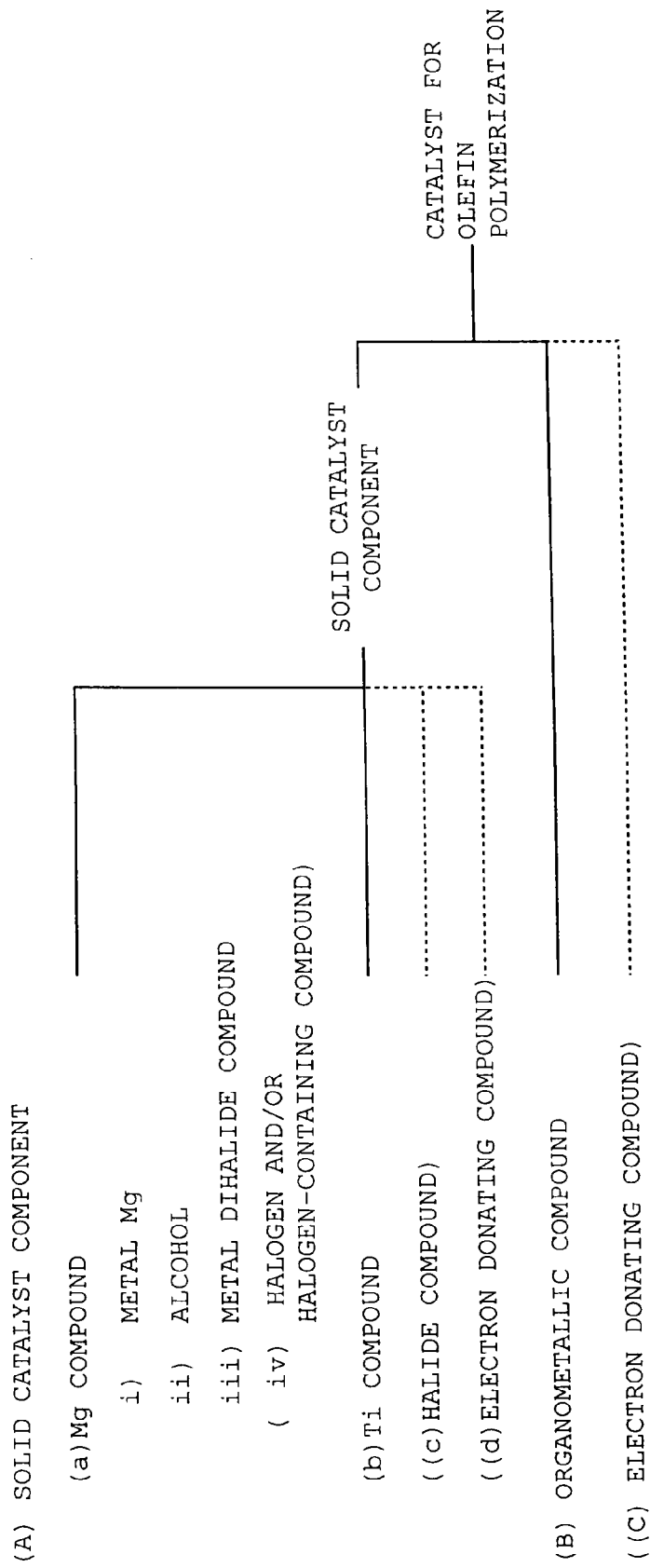
FIG. 1 is a drawing which shows the magnesium compound, the solid catalyst component, and catalyst for olefin polymerization of the invention.

The method of producing an olefin polymer of the invention uses a catalyst for olefin polymerization which contains (A) a solid catalyst component, (B) an organometallic compound, and if necessary, (C) an electron donating compound as a third component.

Now, the catalyst components, method of preparing them, method of polymerization and the like will be explained.

[I] Catalyst Components (A) Solid Catalyst Component

The solid catalyst component can be obtained by reacting a magnesium compound (a), titanium compound (b), and if necessary, a halide (c) and if necessary, an electron donating compound (d).

(a) Magnesium Compound

A magnesium compound is obtained by reacting the following components (i), (ii) and (iii) as essential components, and if necessary, the following component (iv):
(i) metal magnesium
(ii) an alcohol
(iii) a metal dihalide compound represented by the general formula (I) containing at least 0.001 mole of M relative to one mole of magnesium of the metal magnesium (i)

$$MX_2 \tag{I}$$

where X is a halogen atom and M is Mn, Fe, Co or Zn (iv) a halogen and/or a halogen-containing compound containing at least 0.0001 gram atom of a halogen atom relative to one gram atom of magnesium of the metal magnesium (i).

The form and the like of the metal magnesium (i) are not particularly limited and any metal magnesium can be used. The surface state of the metal magnesium is not also particularly limited but metal magnesium without a coating of magnesium hydroxide or the like on the surface thereof is preferred.

Although the kind of the alcohol (ii) is not particularly limited, a lower alcohol having from 1 to 6 carbon atoms is preferably used. Ethanol is preferred since a solid catalyst component that markedly improves catalyst activity can be obtained by using ethanol. Two or more alcohols may be used in combination.

Although the purity and water content of the alcohol (ii) are not particularly limited, when using an alcohol having high water content, magnesium hydroxide is formed on the surface of the metal magnesium, so that an alcohol having a water content of 1% or below, particularly 2,000 ppm or below, is preferably used. Further, morphology improves with decreasing water content, so that an alcohol having a water content of 200 ppm or below is generally preferably.

Although the kind of the halogen of the metal dihalide compound (iii) is not particularly limited, chlorine, bromine or iodine, particularly chlorine, is preferred. Although the kind of metal thereof is not limited, Mn, Fe and Co are preferred. Manganese dichloride, iron dichloride and cobalt dichloride are particularly preferred as the metal dihalide compound. The state, shape, granularity and the like of the halogen-containing compound are not particularly limited, and any compound may be used. For instance, the compound may be used in the state of a solution in an alcohol solvent (for example, ethanol).

The invention uses a halogen and/or the halogen-containing compound (iv) as required. A magnesium compound and polymer powder with a large particle diameter, spherical shape and smooth surface can be preferably produced by the halogen and/or the halogen-containing compound.

Although the kind of the halogen (iv) is not particularly limited, chlorine, bromine or iodine, particularly iodine, is preferred.

The kind of the halogen-containing compound is not limited, and any compound containing a halogen atom other than the metal dihalide compound (iii) may be used. Although the kind of the halogen atom is not particularly limited, chlorine, bromine or iodine is preferred. Among the halogen-containing compounds, halogen-containing metal compounds are particularly preferred. As the halogen-containing compound (iv), specifically, $MgCl_2$, $MgI_2$, $Mg(OEt)Cl$, $Mg(OEt)I$, $MgBr_2$, $CaCl_2$, $NaCl$ and $KBr$ are suitably used. Of these, $MgCl_2$ is particularly preferred. The state, shape, granularity and the like of the halogen-containing compound are not particularly limited, and any compound may be used. For instance, it may be used in the state of a solution in an alcohol solvent (for example, ethanol).

Although the amount of alcohol (ii) is not limited, it is used preferably in an amount of from 2 to 100 mole relative to one mole of the metal magnesium, particularly preferably in an amount of from 5 to 50 mole. When the amount of alcohol (ii) is too large, the yield of the magnesium compound (a) having good morphology may be reduced, and when too small, smooth agitation in a reaction vessel may not be possible. However, it is not limited to the molar ratio mentioned above.

The metal dihalide compound (iii) is used in an amount such that the amount of metal is 0.001 mole or more, preferably 0.005 mole or more, more preferably 0.01 mole or more, particularly preferably 0.02 mole or more, relative to one mole of metal magnesium. When the amount of metal dihalide compound (iii) is less than 0.001 mole atom, the particle diameter of magnesium compound (a) obtained may not sufficiently increase and may not have a spherical shape.

Although the upper limit of the amount of halogen is not particularly limited, the upper limit may be properly selected so long as a desired magnesium compound (a) can be obtained. An upper limit of less than 0.3 mole is generally selected.

The amount of the halogen and/or the halogen-containing compound (iv) as a halogen atom per mole of the metal magnesium is 0.0001 gram atom or more, preferably 0.0005 gram atom or more, more preferably 0.001 gram atom or more. When the amount of the halogen is less than 0.0001 gram atom, there is no difference from a case where halogen is used as a reaction initiator, and when the thus-obtained magnesium compound (a) is used as a catalyst support, the catalyst may be poor in catalyst activity or the olefin polymer may be defective in morphology, and the like. Although the upper limit of the amount of halogen is not particularly limited, the upper limit may be properly selected so long as a desired magnesium compound (a) can be obtained. An upper limit of less than 0.06 gram atom is generally selected.

In the invention, the halogens or the halogen-containing compounds may be used individually or in a combination of two or more halogens or halogen-containing compounds. Further, the halogen and the halogen-containing compound may be used in combination. When the halogen and the halogen-containing compound are used in combination, the amounts thereof are the same as the above-mentioned amounts. In the production method of the invention, the particle diameter of the magnesium compound (a) can freely be controlled by properly selecting the amount of the halogen and/or halogen-containing compound used.

The metal magnesium (i), alcohol (ii), metal dihalide compound (iii) and halogen and/or the halogen-containing compound (iv) can be reacted in a way similar to known ways except for the use of the metal dihalide compound. That is, they are reacted until no more hydrogen gas is generated, usually for 4 to 30 hours, to obtain a magnesium compound.

Specifically, when using manganese dichloride as the metal dihalide compound (iii) and iodine as the halogen (iv), the magnesium compound (a) can be produced by the process of adding iodine in a solid state and manganese dichloride to metal magnesium and alcohol and then reacting the result under heating; of adding the alcohol solution of iodine and the alcohol solution of manganese dichloride dropwise to metal magnesium and alcohol and then reacting the result under heating; and of dropwise adding the alcohol solution of iodine and the alcohol solution of manganese dichloride to metal magnesium and alcohol while heating.

Each method is preferably carried out in the atmosphere of an inert gas (e.g., nitrogen gas or argon gas) and optionally in the presence of an inert organic solvent (e.g., a saturated hydrocarbon such as n-hexane).

Further, it is not required to charge the entire amount of each of the metal magnesium (i), alcohol (ii) metal dihalide compound (iii) and halogen and/or halogen-containing compound (iv) at once from the beginning, and they may be divided and partially charged. In a particularly preferred embodiment, the alcohol is entirely charged in the beginning, the metal magnesium is divided into several portions and such portions are charged separately. In this embodiment, the generation of a large amount of hydrogen gas can be prevented, which is desirable in view of safety. Further, the size of the reaction vessel can be decreased. Further, it is also made possible to prevent the dissipation of alcohol and halogen caused by the momentary generation of a large amount of hydrogen gas. While the number of the portions can be determined by taking account of the size of the reaction vessel and is not specially limited, suitably, each is generally divided into five to ten portions to avoid complicating the procedures.

Further, the reaction may be carried out by either a batch method or a continuous method. Further, there may be employed a variant method in which the entire amount of the metal dihalide compound, the halogen and/or halogen-containing compound and the alcohol is charged in the beginning, a small amount of the metal magnesium is added to the alcohol, the product formed by the reaction is removed by separating it into another vessel, a small amount of the metal magnesium is then charged, and these procedures are repeated.

According to the invention, it is important for the above reaction to use the metal dihalide compound (iii) represented by the formula (I). The use of a compound other than the compound (iii) is not preferred since desired advantages may not be obtained.

When using the thus-obtained magnesium compound (a) for the synthesis of a transition metal compound (A), the dried compound or the compound washed with an inert solvent such as heptane after filtration may be used. In each case, the magnesium compound (a) used for the invention can be used in the following steps without subjecting it to pulverization or classification for uniformizing the particle size distribution. Further, the magnesium compound (a) has a nearly spherical shape, a narrow particle size distribution and a small sphericity variation among the particles. The magnesium compound (a) may be used individually or in a combination of two kinds or more. Further, it may be used in the state supported on a support such as silica, alumina or polystyrene, and as a mixture with a halogen or the like.

Figure 2:
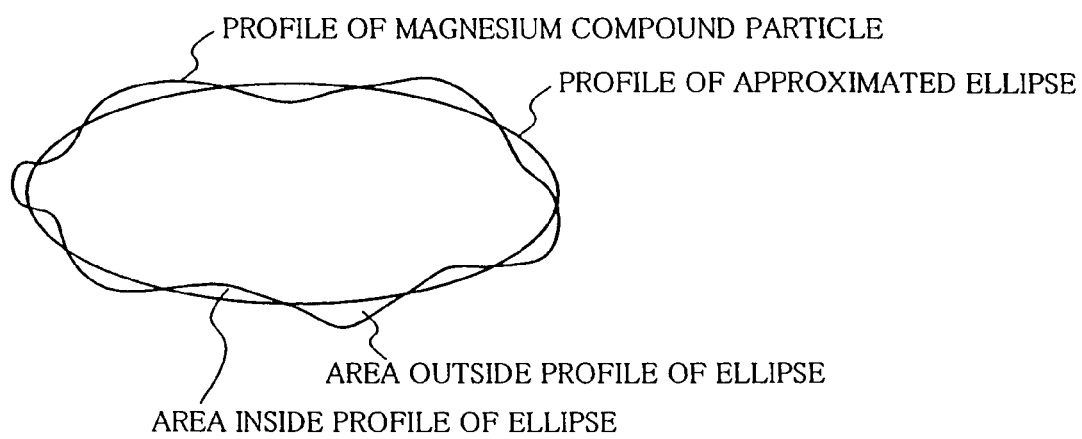
FIG. 2 is a drawing which shows one example of the ellipse approximated to the magnesium compound particle of the invention.

The average particle diameter ($D_{50}$) of the magnesium compound (a) obtained by above mentioned method is preferably 50 μm or more, more preferably 80 μm or more. The sphericity (Sp) represented by the formula (1) is preferably 1.60 or less, more preferably 1.20 or less. The smoothness (Sm) represented by the formula (2) is preferably 1.20 or less, more preferably 1.16 or less.

$$Sp=(L^1/L^2)^3 \quad (1)$$

where $L^1$ is the longest diameter of a projection view of a magnesium compound particle determined by photographing with a scanning electron microscope and thereafter performing image-processing, and $L^2$ is the diameter of a circle which has an area equal to the projection area of the magnesium compound particle.

$$Sm=(L^3/L^4)^3 \quad (2)$$

where $L^3$ is the circumferential length of a projection view of a magnesium compound particle determined by photographing with a scanning electron microscope and thereafter performing image-processing, and $L^4$ is the circumferential length of an ellipse which has an area equal to the projection area of the magnesium compound particle and which is approximated to the profile of the magnesium compound particle such that when the magnesium compound particle is superimposed on the ellipse, the sum of the areas inside and outside the profile of the ellipse among the sections surrounded by the profile of the magnesium compound particle and the profile of the ellipse becomes minimum. Refer to FIG. 2.

The magnesium compound (a) preferably consists essentially of magnesium alkoxide and is solid.

Figure 3:
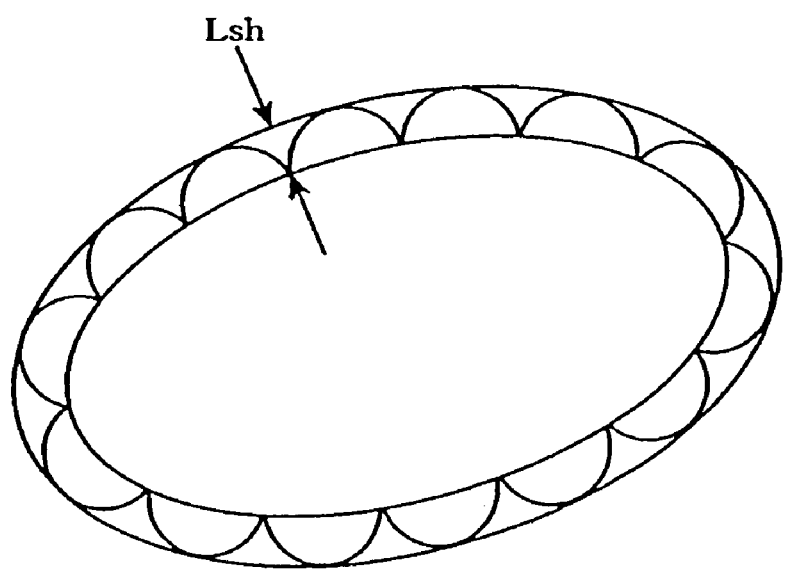
FIG. 3 is a drawing which shows the depth of surface hollows of the magnesium compound particle of the invention.

The magnesium compound (a) preferably has a surface where small spheres connect with each other like a bunch of grapes (FIG. 3). The hollows preferably have a depth (Lsh) of 3 µm or more, more preferably 5 µm. It appears that such a shape enables better mixture of polymer powder and additives used for molding and, for example, can suppress the degradation of quality at the time of molding and decrease in stability of molding in a non-pelletizing process.

(b) Titanium Compound

Although not specially limited, the compound represented by the formula (II) can be preferably used.

$$Ti(OR)_nX_{4-n} \quad (II)$$

where X is a halogen atom, R is a hydrocarbon group having from 1 to 10 carbon atoms, a plurality of which are the same or different to each other, and n is an integer of from 0 to 4.

In the above-mentioned general formula (II), X denotes a halogen atom, and of halogen atoms, preferred is a chlorine atom or a bromine atom and particularly preferred is a chlorine atom. R denotes a hydrocarbon group, which may be a saturated group or an unsaturated group, which may have a straight chain, branched chain or cyclic structure. As R, an alkyl group, an alkenyl group, a cycloalkenyl group, an aryl group, an aralkyl group and the like are preferred, and a straight chain or branched chain alkyl group is particularly preferred. When a plurality of groups as —OR are present, they may be the same as, or different from, each other.

Specific examples of R include methyl, ethyl, n-propyl, isopropyl, n-butyl, sec-butyl, isobutyl, n-pentyl, n-hexyl, n-heptyl, n-octyl, n-decyl, allyl, butenyl, cyclopentyl, cyclohexyl, cyclohexenyl, phenyl, tolyl, benzyl and phenethyl. n is preferably 0 to 1.

Specific examples of the halogen-containing titanium compounds of the above-mentioned general formula (II) include tetraalkoxy titanium such as tetramethoxytitanium, tetraethoxytitanium, tetra-n-propoxytitanium, tetraisopropoxytitanium, tetra-n-butoxytitanium, tetraisobutoxytitanium, tetracyclohexyloxytitanium, and tetraphenoxytitanium; titanium tetrahalides such as titanium tetrachloride, titanium tetrabromide and titanium tetraiodide; alkoxytitanium trihalides such as methoxytitanium trichloride, ethoxytitanium trichloride, propoxytitanium trichloride, n-butoxytitanium trichloride and ethoxytitanium tribromide; dialkoxytitanium dihalides such as dimethoxytitanium dichloride, diethoxytitanium dichloride, diisopropoxytitanium dichloride, di-n-propoxytitanium dichloride and diethoxytitanium dibromide; and trialkoxytitanium monohalides such as trimethoxytitanium chloride, triethoxytitanium chloride, triisopropoxytitanium chloride, tri-n-propoxytitanium chloride and tri-n-butoxytitanium chloride. Of these, high-halogenated titanium compounds are preferred, and titanium tetrachloride is particularly preferred, in view of polymerization activity. These halogen-containing titanium compounds may be used individually or as a combination of two or more compounds.

(c) Halide

The invention may use a halide as required. The use of halide preferably enables the production of an olefin polymer excellent in morphology of the powder with a high activity. The halide includes silicon tetrachloride, silicon tetrabromide, tin tetrachloride and hydrogen chloride, and of these, silicon tetrachloride is particularly preferred. These halides may be used individually or as a combination of two or more halides.

(d) Electron Donating Compound

In the invention, if necessary, an electron-donating compound (d) is employed. The electron-donating compound (d) is preferably used since it may improve the stereoregularity of an olefin polymer to be obtained. The electron-donating compounds (d) include oxygen-containing compounds such as alcohols, phenols, ketones, aldehydes, carboxylic acids, malonic acids, succinic acid, esters of organic acids or inorganic acids and ethers such as monoether, diether and polyether, and nitrogen-containing compounds such as ammonia, amine, nitrile and isocyanate. Of these, esters of polycarboxylic acids are preferred, and esters of aromatic polycarboxylic acids are more preferred. Of these, a monoester and/or a diester of aromatic dicarboxylic acid are/is particularly preferred in view of polymerization activity. Further, the organic groups of the ester portions are preferably a linear, branched or cyclic aliphatic hydrocarbon group.

Specific examples of the electron-donating compounds include dialkyl esters such as methyl, ethyl, n-propyl, isopropyl, n-butyl, isobutyl, t-butyl, n-pentyl, 1-methylbutyl, 2-methylbutyl, 3-methylbutyl, 1,1-dimethylpropyl, 1-methylpentyl, 2-methylpentyl, 3-methylpentyl, 4-methylpentyl, 1-ethylbutyl, 2-ethylbutyl, n-hexyl, cyclohexyl, n-heptyl, n-octyl, n-nonyl, 2-methylhexyl, 3-methylhexyl, 4-methylhexyl, 2-ethylhexyl, 3-ethylhexyl, 4-ethylhexyl, 2-methylpentyl, 3-methylpentyl, 2-ethylpentyl or 3-ethylpentyl dicarboxylates such as phthalate, naphthalene-1,2-dicarboxylate, naphthalene-2,3-dicarboxylate, 5,6,7,8-tetrahydronaphthalene-1,2-dicarboxylate, 5,6,7,8-tetrahydronaphthalene-2,3-dicarboxylate, indan-4,5-dicarboxylate and indan-5,6-dicarboxylate. Of these, phthalic acid diesters are preferred, and phthalic acid diesters in which the organic group of an ester portion is a linear or branched aliphatic hydrocarbon group having 4 or more carbon atoms are particularly preferred.

Preferable specific examples of the phthalic acid diesters include di-n-butyl phthalate, diisobutyl phthalate, di-n-heptyl phthalate and diethyl phthalate and the like. These electron-donating compounds (d) may be used individually or as a combination of two or more compounds.

(B) Organoaluminum Compound

Although not specially limited, the organoaluminum compound (B) can be preferably selected from among an organoaluminum compound having an alkyl group, a halogen atom, a hydrogen atom and an alkoxy group, aluminoxane, or a mixture of these. Specific examples thereof include trialkylaluminum compounds such as trimethylaluminum, triethylaluminum, triisopropylaluminum, triisobutylaluminum and trioctylaluminum; dialkylaluminum monochlorides such as diethylaluminum monochloride, diisopropylaluminum monochloride, diisobutylaluminum monochloride and dioctylaluminum monochloride; alkylaluminum sesquihalides such as ethylaluminum sesquichloride; and linear aluminoxanes such as methylaluminoxane. Of these organoaluminum compounds, trialkylaluminum having a lower alkyl group having 1 to 5 carbon atoms is preferred, and trimethylaluminum, triethylaluminum, tripropylaluminum and triisobutylaluminum are particularly preferred. These organoaluminum compounds (B) may be used individually or as a combination of two or more compounds.

(C) Electron Donating Compound

In the invention, if necessary, an electron donating compound (C) is used. The electron-donating compound (C) is preferably used since it may improve the stereoregularity of an olefin polymer to be obtained. As the electron donating compound, organosilicon compounds having an alkoxy group, nitrogen-containing compounds, phosphorous-containing compounds and oxygen-containing compounds may be used. Of these, it is particularly preferred to use an organosilicon compound having an alkoxy group.

Specific examples of the organosilicon compound having an alkoxy group include trimethylmethoxysilane, trimethylethoxysilane, triethylmethoxysilane, triethylethoxysilane, dimethyldimethoxysilane, dimethyldiethoxysilane, ethylisopropyldimethoxysilane, propylisopropyldimethoxysilane, diisopropyldimethoxysilane, diisobutyldimethoxysilane, isopropylisobutyldimethoxysilane, di-t-butyldimethoxysilane, t-butylmethyldimethoxysilane, t-butylethyldimethoxysilane, t-butylpropyldimethoxysilane, t-butylisopropyldimethoxysilane, t-butylbutyldimethoxysilane, t-butylisobutyldimethoxysilane, t-butyl(s-butyl)dimethoxysilane, t-butylamyldimethoxysilane, t-butylhexyldimethoxysilane, t-butylheptyldimethoxysilane, t-butyloctyldimethoxysilane, t-butylnonyldimethoxysilane, t-butyldecyldimethoxysilane, t-butyl(3,3,3-trifluoromethylpropyl)dimethoxysilane, cyclohexylmethyldimethoxysilane, cyclohexylethyldimethoxysilane, cyclohexylpropyldimethoxysilane, cyclohexylisobutyldimethoxysilane, dicyclohexyldimethoxysilane, cyclohexyl-t-butyldimethoxysilane, cyclopentylmethyldimethoxysilane, cyclopentylethyldimethoxysilane, cyclopentylpropyldimethoxysilane, cyclopentyl-t-butyldimethoxysilane, dicyclopentyldimethoxysilane, cyclopentylcyclohexyldimethoxysilane, bis(2-methylcyclopentyl) dimethoxysilane, bis(2,3-dimethylcyclopentyl) dimethoxysilane, α-naphthyl-1,1,2-trimethylpropyldimethoxysilane, n-tetradecanyl-1,1,2-trimethylpropyldimethoxysilane, 1,1,2-trimethylpropylmethyldimethoxysilane, 1,1,2-trimethylpropylethyldimethoxysilane, 1,1,2-trimethylpropylisopropyldimethoxysilane, 1,1,2-trimethylpropylcyclopentyldimethoxysilane, 1,1,2-trimethylpropylcyclohexyldimethoxysilane, 1,1,2-trimethylpropylmyristyldimethoxysilane, diphenyldimethoxysilane, diphenyldiethoxysilane, phenyltriethoxysilane, methyltrimethoxysilane, methyltriethoxysilane, ethyltrimethoxysilane, ethyltriethoxysilane, propyltrimethoxysilane, isopropyltrimethoxysilane, butyltrimethoxysilane, butyltriethoxysilane, isobutyltrimethoxysilane, t-butyltrimethoxysilane, s-butyltrimethoxysilane, amyltrimethoxysilane, isoamyltrimethoxysilane, cyclopentyltrimethoxysilane, cyclohexyltrimethoxysilane, norbornanetrimethoxysilane, indenyl trimethoxysilane, 2-methylcyclopentyltrimethoxysilane, ethyltriisopropoxysilane, methylcyclopentyl(t-butoxy)dimethoxysilane, isopropyl(t-butoxy)dimethoxysilane, (isobutoxy)dimethoxysilane, t-butyl(t-butoxy)dimethoxysilane, vinyltriethoxysilane, vinyltributoxysilane, chlorotriethoxysilane, γ-chloropropyltrimethoxysilane, γ-aminopropyltriethoxysilane, 1,1,2-trimethylpropyltrimethoxysilane, 1,1,2-trimethylpropylisopropoxydimethoxysilane, 1,1,2-trimethylpropyl(t-butoxy) dimethoxysilane, tetramethoxysilane, tetraethoxysilane, tetrabutoxysilane, tetraisobutoxysilane, ethyl silicate, butyl silicate, trimethylphenoxysilane, methyltriallyloxysilane, vinyltris(β-methoxyethoxy)silane, vinyltrisacetoxysilane and dimethyltetraethoxydisiloxane and the like. These organosilicon compounds may be used individually or as a combination of two or more compounds.

Further, the above organosilicon compound also includes a compound obtained by reacting a silicon compound having no Si—O—C bond with an organic compound having an O—C bond in advance or by reacting these compounds to obtain an organosilicon compound having Si—O—C bond during the polymerization of an α-olefin. Specifically, a compound obtained by reacting silicon tetrachloride and an alcohol is included.

Specific examples of the nitrogen-containing compound include 2,6-substituted piperidines such as 2,6-diisopropylpiperidine, 2,6-diisopropyl-4-methylpiperidine and N-methyl-2,2,6,6-tetramethylpiperidine; 2,5-substituted azolidines such as 2,5-diisopropylazolidine and N-methyl-2,2,5,5-tetramethylazolidine; substituted methylenediamines such as N,N,N',N'-tetramethylmethylenediamine and N,N,N',N'-tetraethylmethylenediamine; and substituted imidazolidines such as 1,3-dibenzylimidazolidine and 1,3-dibenzyl-2-phenylimidazolidine.

Specific examples of the phosphorus-containing compound include phosphorous acid esters such as triethyl phosphite, tri-n-propyl phosphite, triisopropyl phosphite, tri-n-butyl phosphite, triisobutyl phosphite, diethyl-n-butyl phosphite and diethylphenyl phosphite.

Specific examples of the oxygen-containing compound include 2,5-substituted tetrahydrofurans such as 2,2,5,5-tetramethyltetrahydrofuran and 2,2,5,5-tetraethyltetrahydrofuran; and dimethoxymethane derivatives such as 1,1-dimethoxy-2,3,4,5-tetrachlorocyclopentadiene, 9,9-dimethoxyfluorene and diphenyldimethoxymethane.

[II] Preparation of Solid Catalyst Component

As a method of preparing the solid catalyst component (A), the above-mentioned magnesium compound (a), titanium compound (b), and, if necessary, the halide (c) and, if necessary, the electron donating compound (d) may be brought into contact and react with each other. Further, these compounds are preferably brought into contact and react with each other in the amounts thereof under the condition with the operations as follows:

The above-mentioned titanium compound (b) is usually used in an amount within a range of from 0.5 to 100 moles relative to one mole of magnesium of the above-mentioned magnesium compound (a), preferably from 1 to 50 moles. Also, the above-mentioned electron donating compound (d) is usually used in an amount within a range of from 0.01 to 10 moles relative to one mole of magnesium of the magnesium compound (a), preferably from 0.05 to 0.15 mole. Further, as the halide (c), silicon tetrachloride is particularly preferred, and usually used in an amount within a range of from 0.01 to 10 moles relative to one mole of magnesium of the magnesium compound (a), preferably from 0.05 to 2 moles.

The contact temperature is usually within a range of from −20 to 200° C., preferably from 20 to 150° C. The contact period of time is usually from one minute to 24 hours, preferably from 10 minutes to 6 hours.

The procedure of the contact operation is not limited. For instance, the components may be previously brought into contact with each other in the presence of an inert solvent such as a hydrocarbon, or the components previously diluted with an inert solvent such as a hydrocarbon may be brought into contact with each other. The inert solvent includes aliphatic hydrocarbons such as n-pentane, isopentane, n-hexane, n-heptane, n-octane and isooctane; aromatic hydrocarbons such as benzene, toluene and xylene, and mixtures of these hydrocarbons. Furthermore, the contact of titanium compound is preferably carried out two or more times so that the titanium compound is sufficiently supported on the magnesium compound which serves as the catalyst support.

A solid catalyst component obtained by the above contact may be washed with an inert solvent such as a hydrocarbon. The above-mentioned inert solvents may be used. Further, although the washing method is not particularly limited, methods such as decantation and filtration are preferred. Although the amount of the inert solvent used, washing period of time and number of washing times are also not particularly limited, the solvent is usually used in an amount of from 100 to 100,000 mL, preferably from 1,000 to 50,000 mL relative to one mole of the magnesium compound (a), and the contact is usually carried out for one minute to 24 hours, preferably for 10 minutes to 6 hours. When the ratio of the solvent is outside the above-mentioned range, the washing may not be completely carried out.

Although pressure at this time varies depending upon the kind of solvent, the washing temperature and the like, the washing is usually carried out under a pressure within the range of from 0 to 50 kg/cm²G, preferably from 0 to 10 kg/cm²G. Further, during the washing operation, stirring is preferably carried out from the viewpoint of the uniformity of washing and the washing efficiency. The solid catalyst component thus obtained can be stored in the dried state, or in an inert solvent such as a hydrocarbon.

[III] Polymerization

Although the amount of each component of the catalyst in the invention is not especially limited, the solid catalyst component (A) is used in such an amount that the titanium atom amount per liter of a reaction volume is generally in the range of 0.00005 to 1 mmole. The organoaluminum compound (B) is used in such an amount that the aluminum/titanium atomic ratio is generally in the range of from 1 to 1,000, preferably from 10 to 500. When the above atomic ratio is outside the above-mentioned range, the catalyst activity is sometimes insufficient. Further, as a third component, the organosilicon compound (C) is used in such an amount that the electron donating compound (C)/the organoaluminum compound (B) molar ratio is generally in the range of from 0.001 to 5.0, preferably from 0.01 to 2.0, more preferably from 0.05 to 1.0. When the above molar ratio is outside the above range, the sufficient catalyst activity and stereoregularity sometimes cannot be obtained. When a preliminary polymerization is carried out, however, the amount of the organosilicon compound (C) can be further decreased. The olefin used in the invention is preferably the one represented by the following general formula (IV):

$$R^1-CH=CH_2 \quad (IV)$$

In the general formula (IV), $R^1$ is a hydrocarbon or a hydrogen atom and the hydrocarbon group may be saturated or unsaturated, may be linear or branched, or may be cyclic.

Specific examples of the α-olefin include ethylene, propylene, 1-butene, 1-pentene, 1-hexene, 1-heptene, 1-octene, 1-decene, 3-methyl-1-pentene, 4-methyl-1-pentene, vinylcyclohexane, butadiene, isoprene, piperylene, and the like. These olefins may be used solely each, or two or more thereof may be used in combination. Among olefins, ethylene and propylene are particularly preferred.

In the polymerization of an olefin in the invention, the preliminary polymerization of an olefin may be carried out as required before the regular polymerization thereof in view of the polymerization activity, the stereoregularity and powder form of the olefin polymer. In this case, the preliminary polymerization of the olefin is carried out in the presence of a catalyst that is a mixture of predetermined amounts of the solid catalyst component (A), the organoaluminum compound (B) and optionally the electron donating compound (C), generally in the temperature range of from 0 to 100° C. under a pressure of from atmospheric pressure to approximately 5 MPa, and then the regular polymerization of the olefin is carried out in the presence of the catalyst and the preliminary polymerization product.

The polymerization type of the regular polymerization is not especially limited, and any one of solution polymerization, slurry polymerization, gas phase polymerization, bulk polymerization, etc. can be employed. Further, any one of a batch polymerization and a continuous polymerization can be employed, and there can be employed two-step polymerization or multi-step polymerization that is carried out under different conditions.

The reaction condition is not especially limited, the polymerization pressure therefor is optionally selected within a pressure range of generally from atmospheric pressure to 8 MPa, preferably from 0.2 to 5 MPa, and the polymerization temperature is optionally selected within a temperature range of generally from 0 to 200° C., preferably from 30 to 100° C. Although the polymerization time period varies depending upon the kind of olefins or the polymerization temperature so that it cannot be categorically determined, it is generally from 5 minutes to 20 hours, preferably approximately from 10 minutes to 10 hours.

The molecular weight can be adjusted by the addition of a chain transfer agent, preferably the addition of hydrogen. Further, an inert gas such as nitrogen may be present. Alternatively, after the catalyst components (A), (B) and (C) used in the invention are mixed in the predetermined ratio and brought into contact, an olefin may be polymerized at once, or the catalyst components are subjected to maturation for approximately from 0.2 to 3 hours after contact operation, then, an olefin may be polymerized. Further, the catalyst components can be supplied in the state of a suspension in an inert solvent, an olefin or the like. In the invention, aftertreatment of polymerization can be carried out with common procedures. Namely, in the gas phase polymerization, nitrogen gas stream may be passed through the polymer powder taken from the polymerization vessel after polymerization to remove olefins therein, or, if necessary, the polymer may be pelletized with an extrusion machine, and in this regard, a small amount of water, an alcohol or the like may be added in order to completely deactivate the catalyst. In the bulk polymerization, the monomers may be completely separated from the polymer taken from the polymerization vessel after polymerization, followed by pelletizing of the polymer.

EXAMPLES

The invention will be specifically explained with reference to Examples, while the invention shall not be limited to Examples.

In Examples and Comparative Examples, the sphericity (Sp), smoothness (Sm) and average particle diameter ($D_{50}$) of magnesium compound; and sphericity (Sp'), smoothness (Sm'), average particle diameter ($D_{50}$'), isotacticity [mmmm] and angle of repose of polymer powder were measured as follows.

(1) Sphericity (Sp) of Magnesium Compound

A photograph of a dried magnesium compound was taken using a scanning electron microscope (trade name: JSM-25SIII, product of JEOL) of 150 magnifications at an acceleration voltage of 5 KV, to obtain a negative. Then, the negative was image-processed by a transmission method. Particles equivalent to 20 pixels (one pixel covering a 1.389 μm×1.389 μm area) or smaller in area were cut, and the image processing was carried out with an image analyzer (Nexsus Co., Ltd.) with respect to approximately 2,000 particles remaining. The longest diameter $L^1$ of a projection view of a magnesium compound particle and the diameter $L^2$ of a circle which had an area equal to the projection area of the magnesium compound particle were determined, and the sphericity was calculated on the basis of the following expression (1).

$$Sp=(L^1/L^2)^3 \quad (1)$$

(2) Smoothness (Sm) of Magnesium Compound

An image was obtained in the same way as the above (1). Thereafter in a projected view of a magnesium compound particle, an ellipse having an area equal to the projected area of the particle and similar to the particle was superposed on the particle, and the ellipse was approximated such that the sum total of areas inside and outside the profile of the ellipse among the areas of parts defined by the profiles of the ellipse and the particle was the smallest. Circumferential lengths $L^3$ of the particle and circumferential lengths $L^4$ of the ellipse were determined, and the smoothness was calculated on the basis of the following expression (2).

$$Sm=(L^3/L^4)^3 \quad (2)$$

(3) Average Particle Diameter ($D_{50}$) of Magnesium Compound

A magnesium compound was suspended in a hydrocarbon, and in this state, the magnesium compound was measured for particle diameters by a light transmitting method. A particle diameter distribution determined by the measurement was plotted on a logarithmic normal probability paper, and a 50% particle diameter was taken as an average particle diameter ($D_{50}$).

(4) Depth of Surface Hollows (Lsh)

An image was obtained in the same way as (1). As shown in FIG. 3, two ellipses were formed by connecting the most upper part and most under part of each of small spheres connected on the surface. The average of differences between the two profiles of the ellipses was obtained.

(5) Sphericity (Sp') of Polymer Powder

A photograph of a polymer powder was taken with a polarization microscope (trade name: BHS-751P, product of Olympus Corporation) of 40 magnifications and image-processed. The sphericity was calculated by using the expression (1) as in the case of the magnesium compound except that one pixel was changed to 10.4 μm×10.4 μm area and that the image processing was carried out with respect to approximately 300 particles remaining.

(6) Smoothness (Sm') of Polymer Powder

The same measurement as the above (5) was conducted and the smoothness was calculated on the basis of the above-mentioned expression (2).

(7) Average Particle Diameter ($D_{50}$') of Polymer Powder

The particle diameter distribution of polymer powder measured with standard sieves was plotted on a logarithmic normal probability paper, and a 50% particle diameter was taken as an average particle diameter ($D_{50}$).

(8) Isotacticity [mmmm]

A polymer was dissolved in 1,2,4-trichlorobenzene, and isotacticity was determined on the basis of signals of methyl measured at 130° C. by a proton complete decoupling method using a $^{13}$C-NMR (trade name: EX-400, product of JEOL).

An isotactic pentad fraction [mmmm] refers to an isotactic fraction in pentad units of a polypropylene molecule chain determined on the basis of the $^{13}$C-NMR spectrum as proposed by A. Zambelli, et al. on page 925 of Macromolecules, Vol. 6 (1973).

Further, the method of assignment of peaks of $^{13}$C-NMR spectrum was according to the assignment proposed by A. Zambelli, et al. on page 687 of Macromolecules, Vol. 8 (1975).

(9) Angle of Repose of Polymer Powder

A predetermined amount of a sample was caused to drop on a disk, a measurement line was brought into line with the angle of a pile and measured for the angle with a turntable type repose angle measuring apparatus, and the angle was taken as an angle of repose.

(10) [η] Of polymer Powder ([η] Powder)

[η] of polymer powder was determined in tetralin solvent at 135° C. using an auto viscometer (trade name: type VMR-053, product of Rigo Co, LTD.)

(11) [η] of Pellet ([η] Pellet)

100 g of polymer powder and the following additives were fed into a bag made of polyethylene. After mixing well, the mixture was fed into an extruder. The [η] of pellets which were pelletized with a pelletizer was evaluated.

20 φ Single Screw Extruder:
  Die temperature; from 200 to 240° C.
  Resin temperature; from 220 to 230° C.

Additives:
  Irganox 1010 (Ciba Specialty Chemicals): 1,000 ppm
  Calcium stearate (Ciba Specialty Chemicals): 500 ppm
  DHA-4A (Kyowa Chemical Industry Co., Ltd.): 250 ppm
  P-EPQ (Asahi Denka Co., Ltd.): 250 ppm

(12) Δ [η]

Δ [η] was calculated by the following expression.

[η] powder−[η] pellet

The Δ [η] was used as an index of mixture properties of polymer powder and additives. A smaller Δ [η] means less breakage of molecular chains when pelletizing. In the case of small Δ [η], it appears that the mixing property with additives is excellent and the degradation of quality at the time of molding and decrease in stability of molding can be suppressed in a non-pelletizing process.

Example 1

(1) Preparation of Magnesium Compound

A three-necked flask having an internal volume of 0.5 liter and having a stirrer was flushed with nitrogen, and 232 ml (3.95 mole) of dehydrated ethanol (EtOH), 1.9 g (15 mmole) of manganese dichloride, 1.20 g (9.5 milligram atom) of iodine and 12.0 g (0.49 milligram atom) of metal magnesium were poured into the three-necked flask and allowed to react at a reflux temperature (78° C.) with stirring (350 rpm) until no more hydrogen was generated from the system, to give a magnesium compound. It was presumed from the composition analysis and XRD analysis that this magnesium compound was substantially made of diethoxy magnesium and solid in the state where the manganese dichloride poured was absorbed on the surface of plate-like crystal aggregate of diethoxy magnesium. The average particle diameter ($D_{50}$), sphericity (Sp) and smoothness (Sm) of the magnesium compound thus obtained were measured. The results are shown in Table 1.

(2) Preparation of Solid Catalyst Component

A three-necked flask having an internal volume of 0.5 liter and equipped with a stirrer was flushed with nitrogen, and 16 g (0.14 mole) of the magnesium compound obtained in the above (1) and 80 ml of dehydrated octane were placed in the three-necked flask. The mixture was heated to 40° C., and 2.4 ml (23 mmole) of silicon tetrachloride was added. The mixture was stirred for 20 minutes and then added with 3.4 ml (13 mmole) of di-n-butyl phthalate. The resultant solution was temperature-increased up to 80° C., and 77 ml (0.70 mole) of titanium tetrachloride was dropwise added with a dropping funnel. The internal temperature was adjusted to 125° C., and the mixture was stirred for 1 hour, which was defined as a first supporting operation. Then, the reaction product was fully washed with dehydrated octane. Further, 122 ml (1.11 mole) of titanium tetrachloride was added, the internal temperature was adjusted to 125° C., and the mixture was stirred for 2 hours, which was defined as a second supporting operation. Then, the reaction mixture was fully washed with dehydrated octane, to give a transition metal component.

(3) Propylene Slurry Polymerization

An autoclave made of stainless steel having an internal volume of 1 liter and equipped with a stirrer was fully dried and flushed with nitrogen, and 400 ml of dehydrated heptane was placed therein. Further, 2.0 mmole of triethylaluminum was added, then, 0.25 mmole of dicyclopentyldimethoxysilane was added, and the solid catalyst component prepared in the above (2) was added in an amount of 0.0025 mmole per Ti. Hydrogen was introduced up to 0.1 MPa, and then propylene was introduced. Polymerization was carried out for 1 hour at a total pressure of 0.8 MPa and a temperature of 80° C. Then, the temperature was decreased, the pressure was decreased, and the reaction product was taken out and poured into 2 liters of methanol and vacuum-dried to give polypropylene. The isotacticity [mmmm], average particle diameter ($D_{50}'$), sphericity (Sp'), smoothness (Sm') and angle of repose of the polypropylene thus obtained were measured. The results are shown in Table 1.

Example 2

(1) Preparation of Magnesium Compound

Example 1(1) was repeated except that the iodine was replaced with 0.45 g (9.5 milligram atom) of anhydrous magnesium chloride. Table 1 shows the results.

(2) Preparation of Solid Catalyst Component

Example 1(2) was repeated except that the magnesium compound prepared in the above (1) was used.

(3) Propylene Polymerization

Example 1(3) was repeated except that the solid catalyst component obtained in the above (2) was used. Table 1 shows the results.

Example 3

(1) Preparation of Magnesium Compound

Example 1(1) was repeated except that the amount of manganese dichloride was changed to 3.1 g (25 mmole) Table 1 shows the results.

(2) Preparation of Solid Catalyst Component

Example 1(2) was repeated except that the magnesium compound prepared in the above (1) was used.

(3) Propylene Polymerization

Example 1(3) was repeated except that the solid catalyst component obtained in the above (2) was used. Table 1 shows the results.

Example 4

(1) Preparation of Magnesium Compound

Example 1(1) was repeated except that the amount of manganese dichloride was changed to 6.2 g (49 mmole) Table 1 shows the results.

(2) Preparation of Solid Catalyst Component

Example 1(2) was repeated except that the magnesium compound prepared in the above (1) was used.

(3) Propylene Polymerization

Example 1(3) was repeated except that the solid catalyst component obtained in the above (2) was used. Table 1 shows the results.

Example 5

(1) Preparation of Magnesium Compound

Example 1(1) was repeated except that no iodine was added. Table 1 shows the results.

(2) Preparation of Solid Catalyst Component

Example 1(2) was repeated except that the magnesium compound prepared in the above (1) was used.

(3) Propylene Polymerization

Example 1(3) was repeated except that the solid catalyst component obtained in the above (2) was used. Table 1 shows the results.

Example 6

(1) Preparation of Magnesium Compound

Example 1(1) was repeated except that the amount of manganese dichloride was changed to 0.62 g (4.9 mmole). Table 1 shows the results.

(2) Preparation of Solid Catalyst Component

Example 1(2) was repeated except that the magnesium compound prepared in the above (1) was used.

(3) Propylene Polymerization

Example 1(3) was repeated except that the solid catalyst component obtained in the above (2) was used. Table 1 shows the results.

Example 7

(1) Preparation of Magnesium Compound

Example 4(1) was repeated except that the manganese dichloride was replaced with iron dichloride. Table 1 shows the results.

(2) Preparation of Solid Catalyst Component

Example 4(2) was repeated except that the magnesium compound prepared in the above (1) was used.

(3) Propylene Polymerization

Example 4(3) was repeated except that the solid catalyst component obtained in the above (2) was used. Table 1 shows the results.

Example 8

(1) Preparation of Magnesium Compound

Example 4(1) was repeated except that the manganese dichloride was replaced with zinc dichloride. Table 1 shows the results.

(2) Preparation of Solid Catalyst Component

Example 4(2) was repeated except that the magnesium compound prepared in the above (1) was used.

(3) Propylene Polymerization

Example 4(3) was repeated except that the solid catalyst component obtained in the above (2) was used. Table 1 shows the results.

Example 9

(1) Preparation of Magnesium Compound

Example 4(1) was repeated except that the manganese dichloride was replaced with cobalt dichloride. Table 1 shows the results.

(2) Preparation of Solid Catalyst Component

Example 4(2) was repeated except that the magnesium compound prepared in the above (1) was used.

(3) Propylene Polymerization

Example 4(3) was repeated except that the solid catalyst component obtained in the above (2) was used. Table 1 shows the results.

Comparative Example 1

(1) Preparation of Magnesium Compound

A three-necked flask having an internal volume of 0.5 liter and equipped with a stirrer was flushed with nitrogen, and 232 ml (3.95 mole) of dehydrated ethanol (EtOH), 0.72 g (5.7 milligram atom) of iodine and 12 g (0.49 milligram atom) of metal magnesium were poured into the three-necked flask and allowed to react at 70° C. with stirring (350 rpm) until no hydrogen was generated from the system, to give a magnesium compound.

The thus-obtained magnesium compound was evaluated in the same manner as in Example 1(1). Table 1 shows the results.

(2) Preparation of Solid Catalyst Component

Example 1(2) was repeated except that the magnesium compound prepared in the above (1) was used.

(3) Propylene Polymerization

Example 1(3) was repeated except that the solid catalyst component obtained in the above (2) was used. Table 1 shows the results.

Comparative Example 2

(1) Preparation of Magnesium Compound

Comparative Example 1(1) was repeated except that the amount of iodine was changed to 2.4 g (19 milligram atom) and the reaction was carried out at 78° C. with stirring (300 rpm). Table 1 shows the results.

(2) Preparation of Solid Catalyst Component

Example 1(2) was repeated except that the magnesium compound prepared in the above (1) was used.

(3) Propylene Polymerization

Example 1(3) was repeated except that the solid catalyst component obtained in the above (2) was used. Table 1 shows the results.

TABLE 1

| | | unit | Ex. 1 | Ex. 2 | Ex. 3 | Ex. 4 | Ex. 5 | Ex. 6 |
|---|---|---|---|---|---|---|---|---|
| Support | Compound (iii) | | $MnCl_2$ | $MnCl_2$ | $MnCl_2$ | $MnCl_2$ | $MnCl_2$ | $MnCl_2$ |
| | M/Mg | (molar ratio) | 0.03 | 0.03 | 0.05 | 0.10 | 0.10 | 0.01 |
| | Kind of halogen | | $I_2$ | $MgCl_2$ | $I_2$ | $I_2$ | — | $I_2$ |
| | $X_2$ or YX/Mg | (g/atom) | 0.019 | 0.019 | 0.019 | 0.019 | 0 | 0.019 |
| | Reaction Tempreture | (° C.) | 78 | 78 | 78 | 78 | 78 | 78 |
| | Rotation Number | (rpm) | 350 | 350 | 350 | 350 | 350 | 350 |
| | $D_{50}$ | (μm) | 118 | 110 | 133 | 150 | 116 | 51 |
| | Sp | | 1.17 | 1.20 | 1.16 | 1.15 | 1.18 | 1.19 |
| | Sm | | 1.12 | 1.14 | 1.12 | 1.11 | 1.14 | 1.16 |
| | Lsh | (μm) | — | — | — | — | — | — |
| Polymerization | Activity | (kg/g-Cat) | 15.0 | 15.3 | 15.2 | 14.8 | 14.5 | 16.9 |
| | Stereoregularity | (mol %) | 98.2 | 98.3 | 98.4 | 98.2 | 98.2 | 98.3 |
| | $D_{50}'$ | (μm) | 2310 | 2140 | 2470 | 2580 | 2270 | 1390 |
| | Sp' | | 1.16 | 1.18 | 1.15 | 1.14 | 1.18 | 1.19 |
| | Sm' | | 1.08 | 1.10 | 1.07 | 1.05 | 1.10 | 1.14 |
| | Angle of repose | (°) | 38 | 39 | 38 | 37 | 38 | 39 |
| | [η]powder | (g/dL) | — | — | — | — | — | — |
| | [η]pellet | (g/dL) | — | — | — | — | — | — |
| | Δ[η] | (g/dL) | — | — | — | — | — | — |

| | | unit | Ex. 7 | Ex. 8 | Ex. 9 | Comp. Ex. 1 | Comp. Ex. 2 |
|---|---|---|---|---|---|---|---|
| Support | Compound (iii) | | $FeCl_2$ | $ZnCl_2$ | $CoCl_2$ | — | — |
| | M/Mg | (molar ratio) | 0.10 | 0.10 | 0.10 | 0 | 0 |
| | Kind of halogen | | $I_2$ | $I_2$ | $I_2$ | $I_2$ | $I_2$ |
| | $X_2$ or YX/Mg | (g/atom) | 0.019 | 0.019 | 0.019 | 0.011 | 0.038 |

TABLE 1-continued

|   |   |   |   |   |   |   |   |
|---|---|---|---|---|---|---|---|
|  | Reaction Tempreture | (° C.) | 78 | 78 | 78 | 70 | 78 |
|  | Rotation Number | (rpm) | 350 | 350 | 350 | 350 | 300 |
|  | $D_{50}$ | (μm) | 180 | 120 | 124 | 53 | 82 |
|  | Sp |  | 1.13 | 1.19 | 1.16 | 1.35 | 1.37 |
|  | Sm |  | 1.07 | 1.05 | — | 1.26 | 1.27 |
|  | Lsh | (μm) | — | — | 10 | — | — |
| Polymerization | Activity | (kg/g-Cat) | 16.5 | 14.0 | 15.5 | 13.5 | 11.4 |
|  | Stereoregularity | (mol %) | 98.3 | 98.2 | 98.3 | 98.2 | 98.2 |
|  | $D_{50}'$ | (μm) | 3010 | 2280 | 2340 | 1240 | 1530 |
|  | Sp' |  | 1.12 | 1.18 | 1.16 | 1.37 | 1.39 |
|  | Sm' |  | 1.03 | 1.10 | — | 1.28 | 1.28 |
|  | Angle of repose | (°) | 36 | 38 | 40 | 44 | 46 |
|  | [η]powder | (g/dL) | — | — | 1.34 | 1.33 | — |
|  | [η]pellet | (g/dL) | — | — | 1.33 | 1.15 | — |
|  | Δ[η] | (g/dL) | — | — | 0.01 | 0.18 | — |

As shown in Table 1, in Examples there could be produced magnesium compounds with a large particle diameter, smooth surface and spherical shape. In Examples there could also be produced olefin polymers with a large powder particle diameter, smooth surface, spherical shape and high stereoregularity. The polymerization catalysts used in Examples had a high activity.

In a non-pelletizing process where polymer powder and an antioxidant and other such additives are mixed and formed directly without the step of pelletization, the inferior mixing properties of polymer powder and additives may cause breakage of molecular chains. As a result, the quality is degraded and they cannot be stably formed.

In order to enhance the mixing properties, it is desirable for the powder polymer to have powder properties that allow pellet-like handling, such as large particle diameter and high flowability. It is also desirable for the polymer powder to have relatively large surface hollows that enable the mixture of additives. Of the above examples, the polymer powder obtained in the example using $CoCl_2$ shows particularly preferred morphology.

INDUSTRIAL UTILITY

The magnesium compound, the solid catalyst component and the catalyst for olefin polymerization of the invention are usable for a method of producing olefin polymer. The polymer obtained by the method of the invention is excellent in morphology of the polymer powder with a high stereoregularity and can be used in various fields. The polymerization permits omission of a pelletizing step because of the excellent morphology of the polymer powder and enables efficient production of an ethylene-propylene copolymer (for automobile parts etc.) excellent in stiffness, impact resistance and flow property.

The invention claimed is:

1. A method of producing a magnesium compound, comprising reacting the following components (i), (ii) and (iii):
   (i) metal magnesium
   (ii) an alcohol
   (iii) a metal dihalide compound represented by the general formula (I) containing at least 0.001 mole of M relative to one mole of magnesium of the metal magnesium (i)

$$MX_2 \quad (I)$$

where X is a halogen atom and M is Mn, Fe, Co or Zn.

2. The method of producing a magnesium compound according to claim 1, wherein the metal dihalide compound (iii) is manganese dichloride.

3. The method of producing a magnesium compound according to claim 1, wherein the metal dihalide compound (iii) is iron dichloride.

4. The method of producing a magnesium compound according to claim 1, wherein the metal dihalide compound (iii) is cobalt dichloride.

5. The method of producing a magnesium compound according to claim 1, wherein a halogen and/or a halogen-containing compound (iv) containing at least 0.0001 gram atom of a halogen atom relative to one gram atom of magnesium of the metal magnesium (i) is reacted in addition to the components (i), (ii) and (iii), the halogen-containing compound iv not including the metal dihalide compound (iii).

6. The method of producing a magnesium compound according to claim 5, wherein a halogen is reacted and the halogen (iv) is iodine.

7. The method of producing a magnesium compound according to claim 5, wherein a halogen-containing compound is reacted and the halogen-containing compound (iv) is magnesium dichloride.

8. The method of producing a magnesium compound according to claim 1, wherein the magnesium compound has an average particle diameter ($D_{50}$) of 50 μm or more, a sphericity (Sp) represented by the expression (1) of 1.60 or less and a smoothness (Sm) represented by the expression (2) of 1.20 or less:

$$Sp=(L^1/L^2)^3 \quad (1)$$

where $L^1$ is the longest diameter of a projection view of a magnesium compound particle determined by photographing with a scanning electron microscope and thereafter performing image-processing, and $L^2$ is the diameter of a circle which has an area equal to the projection area of the magnesium compound particle;

$$Sm=(L^3/L^4)^3 \quad (2)$$

where $L^3$ is the circumferential length of a projection view of a magnesium compound particle determined by photographing with a scanning electron microscope and thereafter performing image-processing, and $L^4$ is the circumferential length of an ellipse which has an area equal to the projection area of the magnesium compound particle and which is approximated to the profile of the magnesium compound particle such that when the magnesium compound particle is wrapped over the ellipse, the sum of the areas inside and outside the profile of the ellipse among the sections surrounded by the profile of the magnesium compound particle and the profile of the ellipse becomes minimum.

9. The method of producing a magnesium compound according to claim 1, wherein the magnesium compound has an average particle diameter ($D_{50}$) of 50 μm or more, a sphericity (Sp) represented by the expression (1) of 1.60 or less, a depth of surface hollows (Lsh) of 3 μm or more, and a surface where small spheres connect with each other like a bunch of grapes:

$$Sp = (L^1/L^2)^3 \quad (1)$$

where $L^1$ is the longest diameter of a projection view of a magnesium compound particle determined by photographing with a scanning electron microscope and thereafter performing image-processing, and $L^2$ is the diameter of a circle which has an area equal to the projection area of the magnesium compound particle.

10. A method of producing a solid catalyst component comprising the steps of:

(1) producing a magnesium compound (a) by reacting the following components (i), (ii) and (iii):

(i) metal magnesium (ii) an alcohol (iii) a metal dihalide compound represented by the general formula (I) containing at least 0.001 mole of M relative to one mole of magnesium of the metal magnesium (i)

$$MX_2 \quad (1)$$

where X is a halogen atom and M is Mn, Fe, Co or Zn; and (2) reacting the magnesium compound (a) and a titanium compound (b) represented by the general formula (II)

$$Ti(OR)_n X_{4-n} \quad (II)$$

where X is a halogen atom, R is a hydrocarbon group having from 1 to 10 carbon atoms, a plurality of which are the same as or different from each other, and n is an integer of from 0 to 4.

11. The method of producing a solid catalyst component according to claim 10, wherein in the step (2), the following compounds (c) and (d) are reacted in addition to the compounds (a) and (b):

(c) a halide compound (d) an electron donating compound.

12. The method of producing a solid catalyst component according to claim 11, wherein the halogen compound (c) is silicon tetrachloride.

* * * * *